United States Patent

Tenten et al.

Patent Number: 5,686,373
Date of Patent: Nov. 11, 1997

[54] POLYMETAL OXIDE MATERIALS

[75] Inventors: Andreas Tenten, Neustadt; Friedrich-Georg Martin, Heidelberg; Hartmut Hibst, Schriesheim; Laszlo Marosi, Ludwigshafen; Veronika Kohl, Darmstadt, all of Germany

[73] Assignee: BASF Aktiengesellschaft, Ludwigshafen, Germany

[21] Appl. No.: 392,322

[22] Filed: Feb. 22, 1995

[30] Foreign Application Priority Data

Feb. 22, 1994 [DE] Germany .................. 44 05 514.5
Nov. 17, 1994 [DE] Germany .................. 44 40 891.9

[51] Int. Cl.$^6$ .................................. B01J 23/00
[52] U.S. Cl. ................ 502/312; 502/314; 502/315; 502/316; 502/317; 502/318; 502/321; 502/322; 502/323; 502/345; 502/346; 502/353; 558/319; 558/320; 558/321; 558/322; 558/323; 558/324
[58] Field of Search .................. 502/321, 312, 502/314, 315, 316, 317, 318, 322, 323, 345, 346, 353; 558/319–324

[56] References Cited

U.S. PATENT DOCUMENTS 4,035,262 7/1977 Childress et al. .
4,208,306 6/1980 Childress et al. .

FOREIGN PATENT DOCUMENTS

| 0 000 835 | 2/1979 | European Pat. Off. . |
| 0 358 411 | 3/1990 | European Pat. Off. . |
| 0 467 144 | 1/1992 | European Pat. Off. . |
| 0 575 897 | 12/1993 | European Pat. Off. . |
| 2 534 904 | 4/1984 | France . |

*Primary Examiner*—Michael Lewis
*Assistant Examiner*—Thomas G. Dunn, Jr.
*Attorney, Agent, or Firm*—Oblon, Spivak, McClelland, Maier & Neustadt, P.C.

[57] ABSTRACT

Polymetal oxide materials of the general formula I $$[A]_p [B]_q \qquad (I),$$

where

A is $Mo_{12} V_a X^1_b X^2_c X^3_d X^4_e X^5_f X^6_g O_x$  (Co phase),

B is $X^7_{12} Cu_h H_i O_y$  (key phase), $X^1$ is W, Nb, Ta, Cr and/or Ce,
$X^2$ is Cu, Ni, Co, Fe, Mn and/or Zn,
$X^3$ is Sb and/or Bi,
$X^4$ is Li, Na, K, Rb, Cs and/or H,
$X^5$ is Mg, Ca, Sr and/or Ba,
$X^6$ is Si, Al, Ti and/or Zr,
$X^7$ is Mo, W, V, Nb and/or Ta,
a is from 1 to 8,
b is from 0.2 to 5,
c is from 0 to 23,
d is from 0 to 50,
e is from 0 to 2,
f is from 0 to 5,
g is from 0 to 50,
h is from 4 to 30,
i is from 0 to 20, x and y are each a number which is determined by the valency and frequency of the elements other than oxygen in I and p and q are non-zero numbers whose ratio p/q is from 160:1 to 1:1, and their use as catalysts.

65 Claims, No Drawings

POLYMETAL OXIDE MATERIALS

BACKGROUND OF THE INVENTION

1. Description of the Background

The present invention relates to polmetal oxide materials of the general formula I $$[A]_p [B]_q \quad (I),$$

where

A is $MO_{12} V_a X^1_b X^2_c X^3_d X^4_e X^5_f X^6_g O_x$ (Co phase),

B is $X^7_{12} Cu_h H_i O_y$ (key phase), $X^1$ is W, Nb, Ta, Cr and/or Ce, preferably W, Nb and/or Cr, $X^2$ is Cu, Ni, Co, Fe, Mn and/or Zn, preferably Cu, Ni, Co and/or Fe, $X^3$ is Sb and/or Bi, preferably Sb, $X^4$ is Li, Na, K, Rb, Cs and/or H, preferably Na and/or K, $X^5$ is Mg, Ca, Sr and/or Ba, preferably Ca, Sr and/or Ba, $X^6$ is Si, Al, Ti and/or Zr, preferably Si, Al and/or Ti, $X^7$ is Mo, W, V, Nb and/or Ta, preferably Mo, a is from 1 to 8, preferably from 3 to 6, b is from 0.2 to 5, preferably from 0.5 to 2.5, c is from 0 to 23, preferably from 0 to 4, d is from 0 to 50, preferably from 0 to 3, e is from 0 to 2, preferably from 0 to 0.3, f is from 0 to 5, preferably from 0 to 2, g is from 0 to 50, preferably from 0 to 20, h is from 4 to 30, preferably from 6 to 24, particularly preferably from 9 to 18, i is from 0 to 20, preferably from 0 to 10, x and y are each a number which is determined by the valency and frequency of the elements other than oxygen in I and p and q are non-zero numbers whose ratio p/q is from 160:1 to 1:1, preferably from 20:1 to 1:1, particularly preferably from 15:1 to 4:1, which contain the moiety $[A]_p$ in the form of three-dimensional regions A which are delimited relative to their local environment owing to their chemical composition differing from their local environment and have the chemical composition $$A Mo_{12}V_a X^1_b X^2_c X^3_d X^4_e X^5_f X^6_g O_x$$

and the moiety $[B]_q$ in the form of three-dimensional regions B which are delimited relative to their local environment owing to their chemical composition differing from their local environment and have the chemical composition $$B X^7_{12} Cu_h H_i O_y$$

the regions A and B being distributed relative to one another in the same way as in a mixture of finely divided A and finely divided B.

The present invention furthermore relates to processes for the preparation of these materials and to their use.

2. Description of the Background

DE-A 4 335 973 and U.S. Pat. No. 4,035,262 relate to polymetal oxide materials whose gross elemental composition corresponds to that of the novel polymetal oxide materials. These polymetal oxide materials are prepared by processing suitable sources of the components of the desired polymetal oxide materials in the required amounts to give an intimate dry mixture and then calcining the latter at elevated temperature for several hours. The resulting polymetal oxide materials are recommended as catalysts for the preparation of acrylic acid from acrolein by catalytic gas-phase oxidation. However, the disadvantage of the prior art polymetal oxide materials is that, when they are used, the selectivity of the acrylic acid formation for a given acrolein conversion is not completely satisfactory. Furthermore, these polymetal oxide materials exhibit pronounced forming behavior, ie. when freshly prepared polymetal oxide materials are used, the selectivity of the acrylic acid formation (for the given acrolein conversion) reaches its final value only after a relatively long operating time, said final value then being essentially constant. Moreover, the reproducibility of their preparation is unsatisfactory with regard to the constant final value of the selectivity of the acrylic acid formation.

EP-A 835, DE-C 3 338 380, DE-A 4 220 859 and the prior application DE-A 4 307 381 (O.Z. 0050/43890) likewise relate to polymetal oxide materials which are suitable as catalysts for the preparation of α,β-monoethylenically unsaturated carboxylic acids by catalytic gas-phase oxidation and advantageously also have a key phase/Co phase morphology. Although the general formulae of this prior art formally comprise, within a wide variety of possible polymetal oxide materials, also those whose key phase may simultaneously contain the element copper in addition to elements such as molybdenum or tungsten, the totality of all embodiments, however, does not comprise a single such embodiment; rather, said embodiments are restricted to those whose key phase contains the element bismuth instead of the element copper. This embodiment is expressly recommended by the prior art as being particularly preferred. However, the disadvantage of this preferred prior art embodiment is that it too, as a catalyst for the catalytic gas-phase oxidation of acrolein to acrylic acid, is not completely satisfactory with regard to the selectivity of the acrylic acid formation for a given acrolein conversion.

SUMMARY OF THE INVENTION

It is an object of the present invention to provide polymetal oxide materials which do not have the disadvantages of the prior art polymetal oxide materials. We have found that this object is achieved by the materials I defined at the outset.

DESCRIPTION OF THE PREFERRED EMBODIMENTS

Very particularly preferred materials I are those whose regions A have a composition according to the following general formula II $$MO_{12}V_{a'}X^1_{b'}X^2_{c'}X^5_{f'}X^6_{g'}O_{x'} \quad (II),$$

where $X^1$ is W and/or Nb, $X^2$ is Cu and/or Ni, $X^5$ is Ca and/or Sr, $X^6$ is Si and/or Al, a' is from 2 to 6, b' is from 1 to 2, c' is from 1 to 3, f' is from 0 to 0.75, g' is from 0 to 10 and x' is a number which is determined by the valency and frequency of the elements other than oxygen in II.

It is also advantageous if the moiety $[B]_q$ of the novel polymetal oxide materials is present in said materials in the form of three-dimensional regions having the chemical composition B, whose maximum diameters $d_B$ (longest line passing through the locus of the region and connecting two points present on the surface (interface) of the region) are from >0 to 300 μm, preferably from 0.05 to 200 μm, particularly preferably from 0.1 to 50 μm, very particularly preferably from 0.1 to 30 μm. However, the maximum diameters can of course also be from 50 to 150 μm or from 75 to 125 μm (the experimental determination of the maximum diameters can be carried out, for example, by the method of energy-dispersive X-ray analysis (EXDS), for example by means of an electron beam microprobe JEOL JCXA/733).

The moieties $[A]_p$ and $[B]_q$ may be present in amorphous and/or crystalline form in the novel polymetal oxide materials. The moiety $[B]_q$ is preferably crystalline. Preferred polymetal oxide materials are those whose regions B consist essentially of crystallites which have the X-ray diffraction pattern (the structure type) of at least one of the following copper molybdates (the expression in parentheses gives the source of the relevant X-ray diffraction fingerprint):

$Cu_3 (MoO_4)_2 (OH)_2$ (lindgrenite, index card 36-405 of JCPDS-ICDD index (1991)), $Cu_4 Mo_6 O_{20}$ (A. Moini et al., Inorg. Chem. 25 (21) (1986), 3782 to 3785), $Cu_4 Mo_5 O_{17}$ (index card 39-181 of JCPDS-ICDD index (1991)), $Cu_6 Mo_5 O_{18}$ (index card 40-865 of JCPDS-ICDD index (1991)), $Cu_6 Mo_4 O_{15}$ (index card 35-17 of JCPDS-ICDD index (1991)), $Cu Mo O_4$ (index card 22-242 of JCPDS-ICDD index (1991)), $Cu Mo O_4$ (Russian Journal of Inorganic Chemistry 36 (7) (1991), 927-928, Table 1, $CuMoO_4$-III), $Cu_{4-x} Mo_3 O_{12}$ where x=0 to 0.25 (index card 24-56 and 26-547 of JCPDS-ICDD index (1991)), $Cu_3 Mo_2 O_9$ (index card 24-55 and 34-637 of JCPDS-ICDD index (1991)), $Cu_2 Mo O_5$ (index card 22-607 of JCPDS-ICDD index (1991)).

The moiety $[B]_q$ of the novel polymetal oxide materials preferably consists of at least one of these copper molybdates themselves.

Other advantageous novel polymetal oxide materials are those whose regions B contain crystallites of oxometallates of the general formula III $$Cu Mo_A W_B V_C Nb_D Ta_E O_Y \cdot (H_2O)_F \qquad (III),$$

where

1/(A+B+C+D+E) is from 0.7 to 1.3, preferably from 0.85 to 1.15, particularly preferably from 0.95 to 1.05, very particularly preferably 1, F is from 0 to 1, B+C+D+E is from 0 to 1, or from 0 to 0.5, or from 0 to 0.1, and Y is a number which is determined by the valency and frequency of the elements other than oxygen in III, of the structure type which is defined by the compound $CuMoO_4$-III in Russian Journal of Inorganic Chemistry 36 (7) (1991), 927, Table 1. This structure type is referred to therein as wolframite. Checking for the presence of this structure type is done by using the X-ray diffraction pattern.

Crystallites of oxometallates III of the wolframite structure type are referred to below as crystallites B*.

In accordance with the statements just made, crystallites B* which have the stoichiometry $$Cu Mo_A W_B V_C O_Y \qquad (IV),$$

where

1/A+B+C is from 0.7 to 1.3, preferably from 0.85 to 1.15, particularly preferably from 0.95 to 1.05, very particularly preferably 1, and A, B and C are all>0, with the proviso that B+C≤1, are therefore suitable.

Crystallites B* which have the stoichiometry $$Cu Mo_A W_B O_Y \qquad (V),$$

where

1/A+B is from 0.7 to 1.3, preferably from 0.85 to 1.15, preferably from 0.95 to 1.05, very particularly preferably 1, and A and B are both >0, with the proviso that B≤1, are also suitable.

Other suitable crystallites B* are those which have the stoichiometry $$Cu Mo_A V_C O_Y \qquad (VI),$$

where

1/A+C is from 0.7 to 1.3, preferably from 0.85 to 1.15, particularly preferably from 0.95 to 1.05, very particularly preferably 1, and A and C are both>0, with the proviso that C≤1.

In all abovementioned cases, Y is a number which is determined by the valency and frequency of the elements other than oxygen.

Crystallites B* which have the stoichiometry $CuMoO_4$ are also suitable.

The larger the proportion of the crystallites B* in the total moiety of $[B]_q$ of the novel polymetal oxide materials, the more advantageous the resulting novel polymetal oxide materials. The proportion of the crystallites B* is advantageously at least 5, preferably at least 10, particularly preferably at least 25%, by weight, based on the total mass of the moiety $[B]_q$. Preferably, the abovementioned proportion is at least 40, particularly preferably at least 75, very particularly preferably at least 90%, by weight.

An amount of from 95 to 100% by weight is of course is also suitable.

The novel materials I are obtainable in a simple manner, for example by first forming a polymetal oxide material $$X^7_{12} Cu_h H_i O_Y \qquad (B)$$

separately in finely divided form (starting material 1) and then bringing the starting material 1 into intimate contact with suitable sources of the elemental constituents of the polymetal oxide material A $$MO_{12} V_a X^1_b X^2_c X^3_d X^4_e X^5_f X^6_g O_x \qquad (A)$$

in the desired ratio, and calcining a resulting dry mixture at from 250° to 450° C., where the calcination may be carried out under an inert gas (eg. $N_2$), a mixture of inert gas and oxygen (eg. air), a reducing gas, such as a hydrocarbon (eg.

methane), an aldehyde (eg. acrolein) or ammonia, or under a mixture of $O_2$ and a reducing gas (eg. any of the above-mentioned ones), as described, for example, in DE-A 4 335 973 (prior Application O.Z. 0050/44403). In the case of a calcination under reducing conditions, it should be noted that the metallic constituents are not reduced to the element. The calcination time is, as a rule, a few hours and usually decreases with increasing calcination temperature. As is generally known, all that is important with regard to the sources of the elemental constituents of the polymetal oxide material A is that they are either themselves oxides or compounds which are convertible into oxides by heating, at least in the presence of oxygen. In addition to the oxides, other particularly suitable starting compounds are therefore halides, nitrates, formates, oxalates, acetates, carbonates and hydroxides. Suitable starting compounds of Mo, V, W and Nb are also their oxo compounds (molybdates, vanadates, tungstates and niobates) or the acids derived therefrom.

Polymetal oxide materials B can be prepared in a simple manner known per se to those skilled in the art, for example by producing a very intimate, preferably finely divided dry mixture from suitable sources of their elemental constituents and calcining the said mixture at from 200° to 1000° C., preferably from 250° to 600° C., particularly preferably from 300° to 500° C., for several hours, the abovementioned statements being applicable with regard to the calcination time, calcination atmosphere and sources of the elements. In this case, the calcination atmospheres stated there may additionally comprise steam.

The intimate mixing of the starting compounds in the preparation of polymetal oxide materials B can be carried out in the dry or wet state. If effected in the dry state, the starting compounds are advantageously used as finely divided powders and, after mixing and, if required, compaction, are subjected to the calcination. However, intimate mixing is preferably effected in the wet state. The starting compounds are usually mixed with one another in the form of an aqueous solution and/or suspension. Thereafter, the aqueous material is dried and then calcined. The drying process is preferably carried out immediately after the preparation of the aqueous mixture and by means of spray drying (the outlet temperatures are, as a rule, from 100° to 150° C.), which brings about a particularly intimate dry mixture.

It is surprising that crystallites B* grow in the dry process just described, particularly when the stoichiometric composition of the elemental constituents corresponds to that of the general formula III and comprises the element tungsten.

Particularly intimate dry mixtures are obtained in the dry process described when exclusively dissolved sources of the elemental constituents are used as starting materials.

In the case of the elemental constituent copper, it is particularly advantageous in this context to start from aqueous solutions which contain it in the form of copper-ammonia (for example tetramine) complexes.

It is noteworthy that a high proportion of crystallites B* grow in the calcination of such particularly intimate dry mixtures, particularly when they comprise the elemental constituent tungsten and correspond in their stoichiometry of the elemental constituents to the general formula III.

In a preferred method of preparation of the polymetal oxide materials B, the thermal treatment of the intimate mixture of the starting compounds used is carried out in a pressurized vessel (autoclave) in the presence of steam under superatmospheric pressure at from>100° to 600° C. The pressure range is typically up to 500, preferably up to 250, atm. Temperatures above 600° C. and pressures above 500 atm can of course also be used, but this is technologically less advantageous. This hydrothermal treatment is advantageously carried out under conditions under which steam and liquid water coexist. This is possible in the temperature range from>100° C. to 374.15° C. (critical temperature of water) with application of the appropriate pressures. The amounts of water are advantageously such that the liquid phase is capable of taking up the total amount of the starting compounds in suspension and/or solution. However, a procedure in which the intimate mixture of the starting compounds completely absorbs the amount of liquid water in equilibrium with the steam is also possible. Stirring is advantageously carried out during the hydrothermal treatment. Suitable starting compounds for the hydrothermal preparation method are in particular all those which are capable of forming oxides and/or hydroxides when heated under superatmospheric pressure with water. Preferably used starting compounds are oxides and/or hydroxides of the elemental constituents, it being particularly advantageous to start from the oxides of the elements. As a rule, they are used in finely divided form.

In comparison with the preparation by calcination of an intimate dry mixture consisting of sources of the elemental constituents, the result of the hydrothermal method comprises, as a rule, a large proportion of crystallites B*.

If, in the hydrothermal preparation method, the stoichiometric composition of the elemental constituents is chosen according to the general formula III, in general crystallites B* advantageously grow. Crystallites B* are frequently obtained exclusively.

It is surprising that, in the hydrothermal preparation route, crystallites B* grow as a rule even for stoichiometrics of the general formula III which differ from $CuMoO_4$.

The hydrothermal treatment typically takes several hours. After the end of the hydrothermal treatment, the water-insoluble polymetal oxide B can be removed from the autoclave, dried and then converted into a finely divided starting material 1.

The starting material 1 is brought into intimate contact with the sources of the polymetal oxide material A (starting material 2) in either the dry or wet state. In the latter case, it is merely necessary to ensure that the polymetal oxide material B formed beforehand does not dissolve. In an aqueous medium, the latter is usually ensured at a pH which is not too extreme. If said substances are brought into intimate contact in the wet state, the product is usually subsequently dried (preferably spray-dried) to give a dry material. Such a dry material is automatically obtained in a dry mixing procedure.

Examples of possible mixing methods are thus:

a) a dry, finely divided, preformed polymetal oxide B is mixed with dry, finely divided starting compounds of the elemental constituents of the desired polymetal oxide A in the desired ratio in a mixer, kneader or mill;

b) a finely divided polymetal oxide A is formed beforehand by intimate mixing of suitable starting compounds of their elemental constituents (dry or wet), and the resulting intimate dry mixture thereof is then calcined at from 250° to 450° C. (regarding the calcination time, calcination atmosphere and sources of the elements, the statements made on page 8 are applicable); the preformed polymetal oxide A is converted into the finely divided state and mixed with the finely divided preformed polymetal oxide B in the desired ratio as in a); in this mixing method, final calcination of the resulting mixture is not essential;

c) the required amount of the preformed polymetal oxide B is stirred into an aqueous solution and/or suspension of starting compounds of the elemental constituents of the desired polymetal oxide A, and the mixture is then spray-dried; instead of the starting compounds of the elemental constituents of the desired polymetal oxide A it is of course also possible to use a polymetal oxide A itself, which has been formed beforehand according to b).

All mixing methods between a), b) and/or c) can of course also be used. The resulting intimate dry mixture can then be calcined as described and then shaped to the desired catalyst geometry, or vice versa. In principle, the calcined dry mixture (or if required the uncalcined one where mixing method b) is used) can, however, also be used as a powder catalyst.

Our own investigations have shown that, when the dry mixture comprising starting material 1 and starting material 2 is calcined, the preformed polymetal oxide material B is either retained as such (this is the case in particular for a polArmetal oxide B*) or partially or completely converted into other polymetal oxides B. However, there is essentially no fusion of the components of starting material 1 with those of starting material 2.

This makes it possible, after milling of the preformed polymetal oxide B (for example by wet or dry milling, for example in a ball mill or by means of jet milling), to separate off, from the resulting powder generally consisting of essentially spherical particles, the particle class having a maximum particle diameter in the maximum diameter range desired for the material I (as a rule from>0 to 300 µm, preferably from 0.05 to 200 µm, particularly preferably from 0.1 to 50 µm, very particularly preferably from 0.1 to 30 µm), by classification (for example, wet or dry sieving) to be carried out in a manner known per se, and hence to use said particle class in tailored form for the preparation of the desired polymetal oxide material.

When the novel polymetal oxide materials are used as catalysts for the gas-phase catalytic oxidation of acrolein to acrylic acid, shaping to the desired catalyst geometry is preferably effected by application to preshaped inert catalyst carriers, and application may be effected before or after the final calcination. The usual carriers, such as porous or nonporous aluminas, silica, thorium dioxide, zirconiumdioxide, silicon carbide or silicates, such as magnesium silicate or aluminum silicate, may be used. The carriers may have regular or irregular shape, carriers having a regular shape and pronounced surface roughness, for example spheres or hollow cylinders, being preferred. Among these in turn, spheres are particularly advantageous. It is particularly advantageous to use substantially nonporous, spherical steatite carriers which have a rough surface and whose diameter is from 1 to 6 mm, preferably from 4 to 5 mm. The layer thickness of the active material is advantageously chosen to be from 50 to 500 µm, preferably from 150 to 250 µm. It should be pointed out at this point that, to coat the carriers in the preparation of such coated catalysts, the powder material to be applied is as a rule moistened and is dried again after application, for example by means of hot air.

For the preparation of the coated catalysts, coating of the carriers is carried out, as a rule, in a suitable rotatable container, as disclosed in, for example, DE-A 2 909 671 or EP-A 293 859. As a rule, the relevant material is calcined prior to coating of the carrier.

The coating and calcining process according to EP-A 293 859 can be used in a suitable manner so that the resulting polymetal oxide active materials have a specific surface area of from 0.50 to 150 m$^2$/g, a specific pore volume of from 0.10 to 0.90 cm$^3$/g and a pore diameter distribution such that at least 10% of the total pore volume is accounted for by the diameter range from 0.1 to <1 µm, at least 10% by the diameter range from 1.0 to<10 µm and at least 10% by the diameter range from 10 to 100 µm. The pore diameter distributions are preferably brought to those stated in EP-A 293 859 as being preferred.

The novel polymetal oxide materials can of course also be incorporated as unsupported catalysts. For this purpose, the intimate dry mixture comprising the starting materials 1 and 2 is preferably directly compacted to give the desired catalyst geometry (for example pelleting or extrusion), it being possible to add conventional assistants, for example graphite or stearic acid as lubricant and/or molding assistants and reinforcing agents, such as microfibers of glass, asbestos, silicon carbide or potassium titanate, and is calcined. In this case too, in general, calcining can be carried out prior to shaping. A preferred geometry for unsupported catalysts is a hollow cylinder having an external diameter and a length of from 2 to 10 nun and a wall thickness of from 1 to 3 mm.

The novel polymetal oxide materials are particularly suitable as catalysts having high selectivity (for a given conversion) in the gas-phase catalytic oxidation of acrolein to acrylic acid. Usually, acrolein which has been produced by the catalytic gas-phase oxidation of propene is used in the process. As a rule, the acrolein-containing reaction gases from this propene oxidation are used without intermediate purification. The gas-phase catalytic oxidation of the acrolein is usually carried out in tube-bundle reactors as a heterogeneous fixed-bed oxidation. Oxygen, advantageously diluted with inert gases, is used as the oxidizing agent, in a manner known per se. For example, suitable diluent gases are $N_2$, $CO_2$, hydrocarbons, recycled reaction exit gases and/or steam. As a rule, an acrolein:oxygen:steam:inert gas volume ratio of 1:(1 to 3):(0 to 20):(3 to 30), preferably of 1:(1 to 3):(0.5 to 10):(7 to 18) is established in the acrolein oxidation. The reaction pressure is in general from 1 to 3 bar and the total space velocity is preferably from 1000 to 3500 1 (S.T.P.) per 1 per h. Typical multitube fixed-bed reactors are described, for example, in DE-A2 830 765, DE-A 2 201 528 or U.S. Pat. No. 3,147,084. The reaction temperature is usually chosen so that the acrolein conversion is above 90%, preferably above 98%, in a single pass. Reaction temperatures of from 230° to 330° C. are usually required for this purpose.

It is noteworthy that the novel polymetal oxide materials also have a shorter forming time with regard to the selectivity of the acrylic acid formation in the gas-phase catalytic oxidation of acrolein to acrylic acid, ie. if a tube-bundle reactor charged with the novel polymetal oxide materials is operated under the abovementioned conditions using an acrolein-containing gas stream for the purpose of the oxidative formation of acrylic acid, the selectivity of the acrylic acid formation reaches its plateau value within a shorter operating time. The preparation of the novel polymetal oxide materials has high reproducibility with regard to this plateau value.

In addition to the gas-phase catalytic oxidation of acrolein to acrylic acid, the novel products are, however, also capable of catalyzing the gas-phase catalytic oxidation of other organic compounds, in particular other alkanes, alkanols, alkanals, alkenes and alkenols, preferably of 3 to 6 carbon atoms (eg. propylene, methacrolein, tert-butanol, the methyl ether of tert-butanol, isobutene, isobutane or isobutyraldehyde) to olefinically unsaturated aldehydes and/or carboxylic acids and to the corresponding nitriles (ammoxidation, especially of propene to acrylonitrile and of isobutene or tert-butanol to methacrylonitrile). The preparation of acrolein, methacrolein and methacrylic acid may be stated by way of example. However, they are also suitable for the oxidative dehydrogenation of olefinic compounds.

The conversion, selectivity and residence time are defined as follows in this publication, unless stated otherwise:

$$\text{Conversion } C, \text{ based on acrolein (\%)} = \frac{\text{number of moles of converted acrolein}}{\text{number of moles of acrolein used}} \times 100;$$

$$\text{Selectivity } S \text{ of the acrylic acid formation (\%)} = \frac{\text{number of moles of acrolein converted to acrylic acid}}{\text{total number of moles of acrolein converted}} \times 100;$$

$$\text{Residence time (sec)} = \frac{\text{volume of reactor filled with catalyst (l)}}{\text{throughput of synthesis gas } (l(S.T.P.)/h)} \times 3600;$$

EXAMPLES a) Preparation of Novel Polymetal Oxide Materials M and Polymetal Oxide Materials MV for Comparison MV1: 127 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. Thereafter, solution I was stirred all at once into solution II, and the aqueous mixture was spray-dried at an outlet temperature of 110° C. The spray powder was then kneaded with 0.15 kg of water per kg of powder. The paste was calcined in a through-circulation oven fed with an oxygen/nitrogen mixture. The oxygen content was adjusted so that the $O_2$ content at the outlet of the through-circulation oven was 1.5% by volume. In the calcination, the paste was first heated to 300° C. at a rate of 10 K/min and then kept at this temperature for. 6 hours. It was then heated to 400° C. at a rate of 10 K/min and this temperature was maintained for a further hour. In order to establish the ammonia content of the calcination atmosphere, the oven loading O (g of catalyst precursor per 1 of internal volume of the through-circulation oven), the inlet volume flow rate IF (l(S.T.P.)/h) of the oxygen/nitrogen mixture and the residence time RE (sec) of the oxygen/nitrogen feed (ratio of internal volume of through-circulation oven to the volume flow rate of the oxygen/nitrogen mixture fed in) were chosen as listed below. The through-circulation oven used had an internal volume of 3 l.

O: 250 g/l, RE: 135 sec and IF: 80 l(S.T.P.)/h.

The resulting catalytically active material has the following stoichiometry:

After milling of the calcined, catalytically active material to particle diameters of from 0.1 to 50 μm, non-porous steatite spheres having a rough surface and a diameter of from 4 to 5 mn were coated with the resulting active material powder in a rotating drum in an amount of 50 g of powder per 200 g of steatite spheres, with the simultaneous addition of 18 g of water. Drying was then effected with hot air at 110° C.

M1: Starting Material 1:

$Cu_4Mo_6O_{20}$ was prepared in finely divided form (number average particle diameter d̄=8 μm) according to A. Moini et al., Inorg. Chem. 25 (21) (1986), 3782 to 3785, in particular 3782 to 3783.

Starting Material 2:

Aqueous solution of ammonium heptamolybdate tetrahydrate, ammonium metavanadate and ammonium paratungstate heptahydrate in amounts such that the aqueous solution subsequently had the following stoichiometry:

Starting material 1 was stirred into starting material 2 in an amount such that the molar ratio of the abovementioned stoichiometric units was 0.4 (starting material 1):0.8 (starting material 2).

The aqueous mixture was then spray-dried as in MV1 and was further processed to give a coated catalyst.

M2: Starting Material 1:

$Cu_4Mo_5O_{17}$ (index card 39 - 181 of JCPDS-ICDD index (1991)) was prepared in finely divided form (number average particle diameter d̄=8 μm) according to E. M. McCarron III and J. C. Calabrese, J. Solid State Chem. 65 (1986), 215 to 224, in particular 215 to 216.

Starting Material 2:

Aqueous solution as in the case of M1, but having the following stoichiometry:

$Mo_{12}V_{3.6}W_{1.44}$.

Starting material 1 was stirred into starting material 2 in an amount such that the molar ratio of the abovementioned stoichiometric units was 0.4 (starting material 1): 0.83 (starting material 2).

The aqueous mixture was then spray-dried as in MV1 and was further processed to give a coated catalyst.

M3: Starting Material 1:

$Cu_6Mo_5O_{18}$ (index card 40 - 865 of JCPDS-ICDD index (1991)) was prepared in finely divided form (number average particle diameter d̄=8 μm) according to E. M. McCarron III and J. C. Calabrese, J. Solid State Chem. 62 (1986), 64 to 74, in particular 65.

Starting Material 2:

Aqueous solution as in the case of M1, but having the following stoichiometry:

Starting material 1 was stirred into starting material 2 in an amount such that the molar ratio of the abovementioned stoichiometric units was 0.27 (starting material 1): 0.89 (starting material 2).

The aqueous mixture was then spray-dried as in MV1 and was further processed to give a coated catalyst.

M4: Starting Material 1:

$CuMoO_4$ (index card 22 - 242 of JCPDS-ICDD index (1991)) was prepared in finely divided form (number average particle diameter d̄=8 μm) according to K. Nassau and J. W. Shiever, J. Am. Ceram. Soc. 52 (1) (1969), 36 to 40, in particular 36.

Starting Material 2:

Aqueous solution as in the case of M1, but having the stoichiometry $Mo_{12}V_{3.46}W_{1.38}$.

Starting material 1 was stirred into starting material 2 in an amount such that the molar ratio of the abovementioned stoichiometric units was 1.6 (starting material 1):0.87 (starting material 2).

The aqueous mixture was then spray dried as in MV1 and was further processed to give a coated catalyst.

M5: Starting Material 1:

55.3 g of copper(II) oxide (CuO, from Merck, Darmstadt, ultrapure, at least 96%, pulverulent) and 100.0 g of molybdenum(VI) oxide ($MoO_3$, from Merck, Darmstadt, GR, at least 99.5%, pulverulent) were dispersed in 500 ml of water. The total amount of the aqueous dispersion was heated to 350° C. in an autoclave (material: Hastelloy C4, internal volume: 2.5 l) while stirring (1000 revolutions per minute) and was kept at this temperature and at the associated superatmospheric pressure for 24 hours while stirring. Thereafter, the autoclave was cooled to room temperature, the aqueous dispersion contained therein was removed and the dispersed solid was filtered off and then dried in a drying oven at 80° C. Investigation under a scanning electron microscope (SEM) showed that the resulting dry powder had crystalline particles with a number average particle diameter of about 8 μm. The chemical analysis of the crystalline particles gave a Cu/Mo ratio of about 1.

With the use of Cu-Kαradiation (Siemens diffractometer D-5000, 40 kV, 30 mA, with automatic divergence, antiscatter and counter collimator and Peltier detector), the crystalline powder CuMoOy gave the following X-ray diffraction pattern, which is reproduced in the form of interplanar spacings d[Å] independent of the wavelength of the X-rays used, and the associated relative intensities (%), based on the diffraction line having the strongest intensity, of the various diffraction lines:

| d [Å] | Intensity [%] |
|---|---|
| 2.44 | 100 |
| 3.01 | 58.4 |
| 3.14 | 56.8 |
| 2.75 | 35.5 |
| 2.82 | 30.6 |
| 3.39 | 30.1 |
| 1.65 | 25.2 |
| 3.96 | 21.6 |
| 1.72 | 21.1 |
| 2.50 | 20.5 |
| 2.20 | 17.3 |
| 4.68 | 15.2 |
| 2.48 | 14.5 |
| 1.96 | 13.8 |
| 3.71 | 13.7 |
| 3.75 | 13.2 |
| 1.80 | 12.4 |
| 2.90 | 12.2 |
| 2.34 | 12.1 |
| 1.61 | 11.8 |
| 1.59 | 11.6 |
| 3.31 | 11.5 |
| 1.85 | 11.5 |
| 2.04 | 11.3 |
| 2.08 | 11.2 |
| 1.70 | 11.1 |
| 2.00 | 10.8 |
| 1.89 | 10.7 |
| 2.12 | 10.3 |
| 1.88 | 9.15 |
| 1.86 | 8.52 |
| 1.98 | 8.25 |
| 2.30 | 8.01 |
| 2.04 | 7.29 |
| 2.66 | 6.89 |
| 1.57 | 6.73 |
| 1.55 | 6.54 |
| 1.77 | 6.53 |
| 2.37 | 6.45 |
| 1.56 | 6.03 |
| 1.55 | 5.93 |
| 3.45 | 5.82 |
| 2.12 | 5.79 |
| 1.63 | 5.76 |
| 2.06 | 5.72 |
| 1.83 | 5.43 |
| 1.60 | 5.42 |
| 2.14 | 5.12 |
| 5.81 | 4.91 |

The stated interplanar spacings d are accurate to within±0.20 Å (the low-intensity lines presumably also include lines due to minor impurities). This X-ray diffraction pattern corresponds to that for $Cu-MoO_4$-III in Russian Journal of Inorganic Chemistry 36 (7) (1991), 927, Table 1.

Starting Material 2:

A finely divided dry mixture of ammonium heptamolybdate tetrahydrate, ammonium metavanadate and ammonium paratungstate heptahydrate, which had the following stoichiometry:

$$Mo_{12}V_{3.46}W_{1.38}.$$

Starting material 1 was stirred into starting material 2 in an amount such that the molar ratio of the abovementioned stoichiometric units in the resulting dry mixture was 1.6 (starting material 1): 0.87 (starting material 2). The dry mixture was then further processed, in the same way as the spray powder obtained during spray-drying in the case of MV1, to give a coated catalyst.

M6: Starting Material 1:

The finely divided CuMoOy from M5.

Starting Material 2:

The same mixture as in M5, but dissolved in water.

Starting material 1 was stirred into starting material 2 in an amount such that the molar ratio of the abovementioned stoichiometric units was 1.6 (starting material 1): 0.87 (starting material 2).

The aqueous mixture was then spray-dried as in MV1 and was further processed to give a coated catalyst. The latter gave an X-ray diffraction pattern containing the X-ray diffraction pattern of starting material 1.

M7: As in the case of M6, except that starting material M1 was milled to a number average particle size d̄ of 4 μm.

Here too, the resulting coated catalyst gave an X-ray diffraction pattern containing the X-ray diffraction pattern of B*.

M8: As for M6, except that copper(II) acetate monohydrate was additionally stirred into the aqueous mixture prior to spray drying of the latter, in a stoichiometric frequency of copper of 0.8, based on the stoichiometric unit $Mo_{12}V_{3.46}W_{1.38}$ of the material already dissolved in the aqueous mixture.

The aqueous mixture was then spray-dried as in MV1 and was further processed to give a coated catalyst, which likewise gave an X-ray diffraction pattern containing the X-ray diffraction pattern of B*.

MV2: 172.7 g of ammonium molybdate, 43.9 g of ammonium metavanadate and 6.0 g of ammonium dichromate were dissolved in 1400 ml of water. Spatially separated from this, a second solution was prepared from 43.9 g of copper nitrate in 75 ml of water, which had been acidified with 3 ml of concentrated nitric acid. The second solution was then added dropwise to the first solution while stirring and heating. The aqueous mixture was then spray-dried as in MV1 and was further processed to give a coated catalyst. The resulting catalytically active material had the following stoichiometry:

$$Mo_{12}V_{4.6}Cr_{0.56}Cu_{2.22}O_x.$$

M9: Starting Material 1:

The finely divided CuMoOy from M5.

Starting Material 2:

Ammonium molybdate, ammonium metavanadate and ammonium dichromate were dissolved in water in the stoichiometric ratio $Mo_{12}V_{5.6}Cr_{0.69}$.

Starting material 1 was stirred into starting material 2 in an amount such that the molar ratio of the abovementioned stoichiometric units was 2.22 (starting material 1): 0.815 (starting material 2).

The aqueous mixture was then spray-dried as in MV1 and was further processed to give a coated catalyst. The latter gave an X-ray diffraction pattern which contained the X-ray diffraction pattern according to B*.

M10: Starting Material 1:

55.3 g of copper(II) oxide (CuO, from Merck, Darmstadt, ultrapure, at least 96 %, pulverulent), 70.1 g of molybdenum (VI) oxide ($MoO_3$, from Merck, Darmstadt, GR, at least 99.5%), 11.4 g of vanadium(V) oxide ($V_2O_5$, from Merck, Darmstadt, ultrapure, at least 99 and 20.9 g of tungstic acid ($H_2WO_4$, from Merck, Darmstadt, ultrapure, at least 98%) were dispersed in 500 ml of water.

The resulting aqueous dispersion was treated similarly to the preparation of starting material 1 in M5.

An essentially crystalline powder having the stoichiometry $Cu_{50}Mo_{35}V_9W_6O_y$ was obtained, said powder having an X-ray diffraction pattern similar to that of starting material 1 from M5. The number average particle diameter was about 8 μm.

Starting Material 2:

Ammonium molybdate, ammonium metavanadate and ammonium paratungstate were dissolved in water in the stoichiometric ratio $Mo_{12}V_3W_{1.11}$.

Starting material 1 was stirred into starting material 2 in an amount such that the molar ratio of the abovementioned stoichiometric units was 0.91 (starting material 2): 0.032 (starting material 1).

The aqueous mixture was then spray-dried as in MV1 and was further processed to give a coated catalyst. The latter also gave the X-ray diffraction pattern of B*.

MV3: As for M1, except that $Bi_2 Mo_3 O_{12}$ ($\hat{=} Bi_4 Mo_{6 O24}$) according to J. Hinz, Gmelin Mo Supplementary Vol. B1, pages 146 to 157, in particular pages 151 and 152, in appropriately finely divided form, was used as starting material 1.

Furthermore (for stoichiometric reasons), starting material 1 was stirred into starting material 2 in an amount such that the molar ratio of stoichiometric units was 0.8 (starting material 1) : 0.8 (starting material 2).

MV4: as for M4, except that $Bi_2 Mo_2O_9$ ($\hat{=} Bi_4 Mo_4 O_{18}$) according to J. Hinz, Gmelin Mo Supplementary Vol. B1, pages 146 to 157, in particular pages 152 and 153, in appropriately finely divided form, was used as starting material 1.

Furthermore (for stoichiometric reasons), starting material 1 was stirred into starting material 2 in an amount such that the molar ratio of stoichiometric units was 0.8 (starting material 1) : 0.87 (starting material 2).

M11: Starting Material 1:

$Cu_3MO_2O_9$ was prepared in finely divided form (number average particle diameter $\bar{d}$=8 μm) according to T. Machej and J. Ziolkowski, Bull. Acad. Pol. Sci., Ser. Sci. Chim. 24 (1976) 425–431.

Starting Material 2:

Aqueous solution as in the case of M1, but having the stoichiometry:

$Mo_{12} V_{3.29} W_{1.32}$.

Starting material 1 was stirred into starting material 2 in an amount such that the molar ratio of the abovementioned stoichiometric units was 0.53 (starting material 1): 0.91 (starting material 2).

The aqueous mixture was then spray-dried as in MV1 and was further processed to give a coated catalyst.

M12: Starting Material 1:

For the preparation of Cu $MO_{0.74} V_{0.14} W_{0.12} O_{3.93}$, two aqueous mixtures G1 and G2 were first prepared.

G1: At 25° C., 373 g $Cu(CH_3COO)_2 \cdot H_2O$ (Cu content: 32.5% by weight) and 165 g of 25% strength by weight aqueous $NH_3$ solution were stirred in succession into 3 l of water and the resulting mixture was then stirred for a further hour at 25° C.

G2: 248 g of $(NH_4)_6 Mo_7 O_{24} \cdot 4H_2O$ ($MoO_3$ content: 81.3% by weight), 31 g of $NH_4VO_3$ ($V_2O_5$ content: 76.8% by weight) and 62 g of $(NH_4)_{10} W_{12} O_{41} \cdot 7H_2O$ ($WO_3$ content 89.2% by weight) were dissolved in succession in 5 l of water at 90° C. while stirring.

G1 was then stirred into G2, and the resulting aqueous mixture G3 was kept at 80° C. for a further hour while stirring. Thereafter, G3 was spray-dried at an inlet temperature of 310° C. and an outlet temperature of 110° C. 200 g portions of the resulting spray powder were heated from 25° C. to 220° C. in the air in the course of 6 hours in shallow porcelain dishes (linear heating rate) and then left at this temperature in the air for 12 hours. The product preheated at 220° C. was then heated at 400° C. in the air for a further hour and then cooled to 25° C.

An X-ray picture (powder X-ray diffraction pattern) of the resulting powder having the abovementioned stoichiometry was recorded using Cu-$K_\alpha$ radiation. By comparison with known X-ray patterns of known substances, it was possible to assign the powder X-ray diffraction pattern to the following phase composition:

about 65% by weight of a copper molybdate doped with V and W and having the structure $CuMoO_4$-III according to Russian Journal of Inorganic Chemistry 36 (7), (1991), 927, Table 1 (wolframite structure) and about 35% by weight of a copper molybdate doped with V and W and having the structure $CuMoO_4$ according to index card 22-242 of JCPDS-ICDD index (1991).

Starting Material 2:

Aqueous solution as in the case of M1, but having the following stoichiometry:

$Mo_{12} V_{3.09} W_{1.10}$.

Starting material 1 was stirred into starting material 2 in an amount such that the molar ratio of the abovementioned stoichiometric units was 1.6 (starting material 1): 0.90 (starting material 2).

The aqueous mixture was then spray-dried as in MV1 and was further processed to give a coated catalyst. The latter likewise gave an X-ray diffraction pattern containing the X-ray diffraction pattern of the wolframite type.

M13: Starting Material 1:

For the preparation of $CuMo_{0.75} W_{0.25} O_4$, the procedure was the same as that for the preparation of starting material 1 in M12. However, the compositions of G1 and G2 were:

G1: 456 g of $Cu(CH_3COO)_2 \cdot H_2O$ (Cu content: 32.5% by weight), 128 g of 25% strength by weight aqueous $NH_3$ solution and 3 l of $H_2O$.

G2: 310 g of $(NH_4)_6 Mo_7 O_{24} \cdot 4H_2O$ ($MoO_3$ content: 81.3% by weight), 151 g of $(NH_4)_{10} W_{12} O_{41} \cdot 7H_2O$ ($WO_3$ content: 89.2% by weight) and 5 l of H20.

In addition, subsequent heating in air was carried out at 500° C. for 1 hour instead of at 400° C. for 1 hour.

An X-ray picture (powder X-ray diffraction pattern) of the resulting powder having the abovementioned stoichiometry was recorded using Cu-K$_\alpha$ radiation. By comparison with known X-ray patterns of known substances, it was possible to assign the powder X-ray diffraction pattern to the following phase composition:

about 50% by weight of a copper molybdate doped with W and having the structure of the CuMoO$_4$-III according to Russian Journal of Chemistry 36 (7), (1991), 927, Table 1 (wolframite structure) and about 50% by weight of a copper molybdate doped with W and having the structure CuMoO$_4$ according to index card 22-242 of JCPDS-ICDD index (1991).

Starting Material 2:

Aqueous solution as in the case of M1, but having the following stoichiometry:

$Mo_{12} V_{3.33} W_{0.89}$. 

Starting material 1 was stirred into starting material 2 in an amount such that the molar ratio of the abovementioned stoichiometric units was 1.6 (starting material 1):0.90 (starting material 2).

The aqueous mixture was then spray-dried as in MV1 and was further processed to give a coated catalyst. The latter likewise gave an X-ray diffraction pattern containing the X-ray diffraction pattern of the wolframite type.

M14:Starting Material 1:

For the preparation of CuMo$_{0.5}$ W$_{0.5}$ O$_4$, the procedure was the same as that for the preparation of starting material 1 in M12. However, the compositions of G1 and G2 were:

G1: 493 g of Cu(CH$_3$COO)$_2$ . H$_2$O (Cu content: 32.5% by weight), 198 g of 25% by weight aqueous NH$_3$ solution and 3 l of H$_2$O.

G2: 223 g of (NH$_4$)$_6$ Mo$_7$ O$_{24}$ . 4H$_2$O ( MoO$_3$ content: 81.3 % by weight ), 327 g of (NH$_4$)$_{10}$ W$_{12}$ O$_{41}$ . 7H$_2$O (WO$_3$ content: 89.2% by weight) and 5 l of H$_2$O.

In addition, subsequent heating in air was carried out at 500° C. for 1 hour instead of at 400° C. for 1 hour.

An X-ray picture (powder X-ray diffraction pattern) of the resulting powder having the abovementioned stoichiometry was recorded using Cu-K$_\alpha$ radiation. The powder proved to have a single phase. It consisted completely of the wolframite structure (structure type of CuMoO$_4$-III according to Russian Journal of Inorganic Chemistry36 (7), (1991), 927, Table 1).

Starting Material 2:

Aqueous solution as in the case of M1, but having the following stoichiometry:

$Mo_{12} V_{3.21} W_{0.43}$. 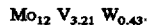

Starting material 1 was stirred into starting material 1 in an amount such that the molar ratio of the abovementioned stoichiometric units was 1.6 (starting material 1) : 0.93 (starting material 2).

The aqueous mixture was then spray-dried as in MV1 and was further processed to give a coated catalyst. The latter likewise gave an X-ray diffraction pattern containing the X-ray diffraction pattern of the wolframite type.

M15:As for M12, except that, the preparation of the starting material 1, 435 g of 25% strength by weight aqueous NH$_3$ solution was used for the preparation of mixture G1, instead of 165 g of 25% strength by weight aqueous NH$_3$ solution.

In addition, 200 g portions of the resulting spray powder were heated from 25° C. to 300° C. in the air in the course of 3 hours in shallow porcelain dishes (linear heating rate) and then left at this temperature in the air for 1 hour. Thereafter, the product preheated at 300° C. was heated at 400° C. in the air for a further hour and then cooled to 25° C.

An X-ray picture (powder X-ray diffraction pattern) of the powder thus obtained as starting material 1 and having the stoichiometry CUMo$_{0.74}$ V$_{0.14}$ W$_{0.12}$ O$_{3.93}$ was recorded using Cu-K$_\alpha$ radiation. By comparison with known X-ray patterns of known substances, it was found that the powder contained>95% by weight of a copper molybdate doped with V and W and having the structure of the CuMoO$_4$-III according to Russian Journal of Inorganic Chemistry36 (7) (1991), 927, Table 1 (wolframite structure).

b) Use of Coated Catalysts from a) as Catalysts for the Gas-Phase Oxidation of Acrolein into Acrylic Acid The catalysts were introduced into a tube reactor (V2A stainless steel, 25 mm internal diameter, 2000 g catalyst bed, thermostated with salt bath) and were fed with a gaseous mixture composed of 5% by volume of acrolein, 7% by volume of oxygen, 15% by volume of steam and 73% by volume of nitrogen at reaction temperatures of from 250° to 270° C. using a residence time of 2.0 sec. In all cases, the salt bath temperature was adjusted so that, after forming was complete, a standard acrolein conversion C of 99% resulted during a single pass. The product gas mixture flowing out of the tube reactor was analyzed by gas chromatography. The results for the selectivity of the acrylic acid formation using the various catalysts are shown in the table below.

| Catalyst | S (%) |
| --- | --- |
| MV1 | 95.3 |
| M1 | 95.4 |
| M2 | 95.4 |
| M3 | 95.6 |
| M4 | 95.7 |
| M5 | 95.5 |
| M6 | 95.9 |
| M7 | 96.0 |
| M8 | 96.0 |
| M10 | 95.8 |
| MV2 | 93.4 |
| M9 | 93.9 |
| MV3 | 92.6 |
| MV4 | 92.2 |
| M11 | 95.5 |
| M12 | 96.5 |
| M13 | 96.5 |
| M14 | 96.0 |
| M15 | 96.8 |

We claim:

1. A polymetal oxide material of the formula I $$[A]_p [B]_q \qquad (I),$$

where

A is $MO_{12} V_a X^1_b X^2_c X^3_d X^4_e X^5_f X^6_g O_x$  (Co phase), 

B is $X^7_{12} Cu_h H_i O_y$  (key phase), $X^1$ is W, Nb, Ta, Cr and/or Ce, $X^2$ is Cu, Ni, Co, Fe, Mn and/or Zn, $X^3$ is Sb and/or Bi, $X^4$ is Li, Na, K, Rb, Cs or H, $X^5$ is Mg, Ca, Sr or Ba, $X^6$ is Si, Al, Ti or Zr, $X^7$ is Mo, W, V, Nb or Ta, a is from 1 to 8, b is from 0.2 to 5, c is from 0 to 23, d is from 0 to 50, e is from 0 to 2, f is from 0 to 5, g is from 0 to 50, h is from 4 to 30, i is from 0 to 20, x and y are each a number which is determined by the valency and frequency of the elements other than oxygen in I and p and q are non-zero numbers whose ratio p/q is from 160:1 to 1:1, which contains the moiety $[A]_p$ in the form of three-dimensional regions A which are delimited from their local environment owing to their chemical composition differing from their local environment and have the chemical composition $$A\ Mo_{12}V_a X^1_b X^2_c X^3_d X^4_e X^5_f X^6_g O_x$$

and the moiety $[B]_q$ in the form of three-dimensional regions B which are delimited relative-to-their local environment owing to their chemical composition differing from their local environment and have the chemical composition $$B\ X^7_{12} Cu_h H_i O_y$$

the regions A and B being distributed relative to one another in the same way as in a mixture of finely divided A and finely divided B.

2. A polymetal oxide material as claimed in claim 1, where $X^1$ is W, Nb or Cr.

3. A polymetal oxide material as claimed in claim 1 or 2, where $X^2$ is Cu, Ni, Co or Fe.

4. A polymetal oxide material as claimed in claim 1, where $X^3$ is Sb.

5. A polymetal oxide material as claimed in claim 1, where $X^4$ is Na or K.

6. A polymetal oxide material as claimed in claim 1, where $X^5$ is Ca, Sr or Ba.

7. A polymetal oxide material as claimed in claim 1, where $X^6$ is Si, Al or Ti.

8. A polymetal oxide material as claimed in claim 1, where $X^7$ is Mo.

9. A polymetal oxide material as claimed in claim 1, where a is from 3 to 6.

10. A polymetal oxide material as claimed in claim 1, where b is from 0.5 to 2.5.

11. A polymetal oxide material as claimed in claim 1, where c is from 0 to 4.

12. A polymetal oxide material as claimed in claim 1, where d is from 0 to 3.

13. A polymetal oxide material as claimed in claim 1, where e is from 0 to 0.3.

14. A polymetal oxide material as claimed in claim 1, where f is from 0 to 2.

15. A polymetal oxide material as claimed in claim 1, where g is from 0 to 20.

16. A polymetal oxide material as claimed in claim 1, where h is from 6 to 24.

17. A polymetal oxide material as claimed in claim 1, where h is from 9 to 17.

18. A polymetal oxide material as claimed in claim 1, where p/q is from 20:1 to 1:1.

19. A polymetal oxide material as claimed in claim 1, where p/q is from 15:1 to 4:1.

20. A polymetal oxide material as claimed in claim 1, whose regions A have a composition of the formula II $$Mo_{12}V_{a'} X^1_{b'} X^2_{c'} X^5_{f'} X^6_{g'} O_{x'} \quad (II),$$

where $X^1$ is W or Nb, $X^2$ is Cu or Ni, $X^5$ is Ca or Sr, $X^6$ is Si or Al, a' is from 2 to 6, b' is from 1 to 2, c' is from 1 to 3, f' is from 0 to 0.75, g' is from 0 to 10 and X' is a number which is determined by the valency and frequency of the elements other than oxygen in II.

21. A polymetal oxide material as claimed in claim 1, which contains the moiety $[B]_q$ in the form of three-dimensional regions which have the chemical composition B and whose maximum diameter $d_B$ is from >0 to 300 pa.

22. A polymetal oxide material as claimed in claim 1, which contains the moiety $[B]_q$ in the form of three-dimensional regions which have the chemical composition B and whose maximum diameter $d_B$ is from 0.05 to 200 µm.

23. A polymetal oxide material as claimed in claim 1, which contains the moiety $[B]_q$ in the form of three-dimensional regions which have the chemical composition B and whose maximum diameter $d_B$ is from 0.1 to 50 µm.

24. A polymetal oxide material as claimed in claim 1, which contains the moiety $[B]_q$ in the form of three-dimensional regions which have the chemical composition B and whose maximum diameter $d_B$ is from 0.1 to 30 µm.

25. A polymetal oxide material as claimed in claim 1 to 24, whose regions B contain crystallites which have the X-ray diffraction pattern of at least one of the following copper molybdates:

$Cu_3 (MoO_4)_2 (OH)_2$, $Cu_4 Mo_6 O_{20}$, $Cu_4 Mo_5 O_{17}$, $Cu_6 Mo_5 O_{18}$, $Cu_6 Mo_4 O_{15}$, $Cu\ Mo\ O_4$, $CuMoO_4$, $Cu_{4-x} Mo_3 O_{12}$ where x=0 to 0.25, $Cu_3 Mo_2 O_9$, $Cu_2 Mo O_5$.

26. A polymetal oxide material as claimed in claim 1, whose regions B contain crystallites B* of oxometallates of the formula III $$Cu\ Mo_A W_B V_C Nb_D Ta_E O_Y \cdot (H_2O)_F \quad (III),$$

where $1/(A+B+C+D+E)$ is from 0.7 to 1.3,

F is from 0 to 1, $B+C+D+E$ is from 0 to 1 and

Y is a number which is determined by the valency and frequency of the elements other than oxygen in III, selected from the group consisting of wolframite and distorted wolframite.

27. A polymetal oxide material as claimed in claim 26, where 1/(A+B+C+D+E) is from 0.85 to 1.15.

28. A polymetal oxide material as claimed in claim 26, where 1/(A+B+C+D+E) is from 0.95 to 1.05.

29. A polymetal oxide material as claimed in claim 26, where 1/(A+B+C+D+E) is 1.

30. A polymetal oxide material as claimed in claim 1, where F is 0.

31. A polymetal oxide material as claimed in claim 1, where B+C+D+E is from 0 to 0.5.

32. A polymetal oxide material as claimed in claim 31, where B+C+D+E is from 0 to 0.1.

33. A polymetal oxide material as claimed in claim 31, where B+C+D+E is 0.

34. A polymetal oxide material as claimed in claim 1, whose regions B contain crystallites B* of polymetal oxides of the formula IV $$CuMo_A W_B V_C O_Y \qquad (IV)$$

where

1/A+B+C is from 0.7 to 1.3,

A, B and C are all>0, with the proviso that B+C≦1, and

Y is a number which is determined by the valency and frequency of the elements other than oxygen in (IV)

selected from the group consisting of wolframite and distorted wolframite.

35. A polymetal oxide material as claimed in claim 1, whose regions B contain crystallites B* of polymetal oxides of the formula V $$Cu Mo_A W_B O_Y \qquad (V)$$

where

1/A+B is from 0.7 to 1.3,

A and B are all>0, with the proviso that B≦1, and

Y is a number which is determined by the valency and frequency of the elements other than oxygen in (V)

selected from the group consisting of wolframite and distorted wolframite.

36. A polymetal oxide material as claimed in claim 1, whose regions B contain crystallites B* of polymetal oxides of the formula VI $$Cu Mo_A V_C O_Y \qquad (V)$$

where

1/A+C is from 0.7 to 1.3,

A and C are all>0, with the proviso that C≦1, and

Y is a number which is determined by the valency and frequency of the elements other than oxygen in (VI)

selected from the group consisting of wolframite and distorted wolframite.

37. A polymetal oxide material as claimed in claim 26, in which the proportion of the crystallites B* is at least 5% by weight, based on the total mass of the moiety $[B]_q$.

38. A polymetal oxide material as claimed in claim 26, in which the proportion of the crystallites B* is at least 50% by weight, based on the total mass of the moiety $[B]_q$.

39. A polymetal oxide material as claimed in claim 26, in which the proportion of the crystallites B* is at least 75% by weight, based on the total mass of the moiety $[B]_q$.

40. A polymetal oxide material as claimed in claim 26, in which the proportion of the crystallites B* is at least 90% by weight, based on the total mass of the moiety $[B]_q$.

41. A polymetal oxide material as claimed in claim 26, in which the proportion of the crystallites B* is from 95 to 100% by weight, based on the total mass of the moiety $[B]_q$.

42. A polymetal oxide material as claimed in claim 26, whose crystallite B* has the stoichiometry $CuMoO_4$.

43. A polymetal oxide material of the formula III $$CuMo_A W_B V_C Nb_D Ta_E O_Y (H_2O)_F \qquad (III)$$

where

1/(A+B+C+D+E) is from 0.7 to 1.3,

F is from 0 to 1

B+C+D+E is from>0 to 1 and

Y is a number which is determined by the valency and frequency of the elements other than oxygen in III, whose structure type is selected from the group consisting of wolframite and distorted wolframite.

44. A polymetal oxide material as claimed in claim 43, where (A+B+C+D+E) is from 0.85 to 1.15.

45. A polymetal oxide material as claimed in claim 43 where (A+B+C+D+E) is from 0.95 to 1.05.

46. A polymetal oxide material as claimed in claim 43, where (A+B+C+D+E) is 1.

47. A polymetal oxide material as claimed in claim 43 where F is 0.

48. A polymetal oxide material as claimed in claim 43, where B+C+D+E is from>0 to 0.5.

49. A polymetal oxide material as claimed in claim 43, where B+C+D+E is from>0 to 0.1.

50. A polymetal oxide material of the formula IV $$Cu Mo_A W_B V_C O_Y \qquad (IV)$$

where

A+B+C is from 0.7 to 1.3,

A, B and C are all>0, with the proviso that B+C≦1, and

Y is a number which is determined by the valency and frequency of the elements other than oxygen in (IV), whose structure type is selected from the group consisting of wolframite and distorted wolframite.

51. A polymetal oxide material of the formula V $$Cu Mo_A W_B O_Y \qquad (V)$$

where

1/A+B is from 0.7 to 1.3,

A and B are all>0, with the proviso that B≦1, and

Y is a number which is determined by the valency and frequency of the elements other than oxygen in (VI), whose structure type is selected from the group consisting of wolframite and distorted wolframite.

52. A polymetal oxide material of the formula VI $$Cu Mo_A V_C O_Y \qquad (VI)$$

where

1/A+C is from 0.7 to 1.3,

A and C are all >0, with the proviso that C≦1, and

Y is a number which is determined by the valency and frequency of the elements other than oxygen in (VI), whose structure type is selected from the group consisting of wolframite and distorted wolframite.

53. A process for the preparation of a polymetal oxide material as claimed in claim 43, wherein sources of the elements constituting the polymetal oxide material are intimately mixed with one another, and the resulting intimate mixture is thermally treated in a pressurized vessel at from >100° to 600° C. in the presence of steam under superatmospheric pressure.

54. A process as claimed in claim 53, wherein the hydrothermal treatment is carried out under conditions under which steam and liquid water are capable of coexisting.

55. A process as claimed in claim 53 or 54, wherein the coexisting liquid aqueous phase is capable of taking up the total amount of starting mixture in suspension or solution.

56. A process as claimed in claim 53, wherein exclusively oxides or hydroxides are used as sources.

57. A process as claimed in claim 53, wherein the stoichiometric composition of the elemental constituents in the starting mixture corresponds to that of the formula (III') in claim 43.

58. A process for the preparation of polymetal oxide material B whose stoichiometry corresponds to one of the formula (III'), (IV), (V) or (VI) as claimed in any of claims 43, 34, 35 and 36, where an intimate dry mixture is produced from sources of their elemental constituents and said mixture is calcined at from 200° to 1000° C.

59. A process as claimed in claim 58 where the sources of the elemental constituents comprise the element tungsten.

60. A process as claimed in claim 58, wherein the intimate dry mixture is produced by mixing the sources of the elemental constituents with one another in aqueous solution or suspension and then spray-drying the aqueous mixture.

61. A process as claimed in any of claim 58, wherein exclusively dissolved sources of the elemental constituents are used as starting materials for producing the intimate dry mixture.

62. A process as claimed in claim 58, wherein the elemental constituent copper in the form of copper-ammonia complexes present in aqueous solution is used for producing the intimate dry mixture.

63. A process for the preparation of a polymetal oxide material as claimed in claim 1, wherein a polymetal oxide material

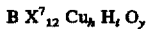

is formed beforehand separately in finely divided form (starting material 1) and starting material 1 is then brought into intimate contact with suitable sources of the elemental constituents of a polymetal oxide material A

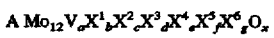

in the desired ratio, and a resulting dry mixture is calcined at from 250° to 450° C.

64. A process for the preparation of a polymetal oxide material as claimed in claim 1, wherein the polymetal oxide material of claim 43 is used.

65. A process for the preparation of acrylic acid from acrolein which comprises reacting acrolein with oxygen by gas-phase catalytic oxidation in the presence of a catalyst, wherein the catalyst used is a polymetal oxide material as claimed in claim 1.

* * * * *